(12) United States Patent
Tao et al.

(10) Patent No.: US 8,465,634 B2
(45) Date of Patent: Jun. 18, 2013

(54) SYSTEMS AND METHODS FOR INTEGRATED ELECTROCHEMICAL AND ELECTRICAL DETECTION

(75) Inventors: Nongjian Tao, Scottsdale, AZ (US); Erica Forzani, Mesa, AZ (US)

(73) Assignee: Arizona Board of Regents, Scottsdale, AZ (US)

( * ) Notice: Subject to any disclaimer, the term of this patent is extended or adjusted under 35 U.S.C. 154(b) by 669 days.

(21) Appl. No.: 12/601,211

(22) PCT Filed: May 23, 2008

(86) PCT No.: PCT/US2008/064744
§ 371 (c)(1),
(2), (4) Date: May 20, 2010

(87) PCT Pub. No.: WO2008/148025
PCT Pub. Date: Dec. 4, 2008

(65) Prior Publication Data
US 2010/0253370 A1    Oct. 7, 2010

Related U.S. Application Data

(60) Provisional application No. 60/939,738, filed on May 23, 2007.

(51) Int. Cl.
*G01N 27/403* (2006.01)
*G01N 27/327* (2006.01)

(52) U.S. Cl.
USPC ............... 204/400; 204/431; 204/403.01

(58) Field of Classification Search
USPC ............... 204/400, 403.01–403.15, 416–418, 204/431; 257/253
See application file for complete search history.

(56) References Cited

U.S. PATENT DOCUMENTS

| | | | |
|---|---|---|---|
| 4,338,157 A | 7/1982 | Kanda | |
| 4,721,601 A * | 1/1988 | Wrighton et al. | 422/82.03 |
| 5,288,636 A * | 2/1994 | Pollmann et al. | 204/403.14 |
| 5,580,433 A | 12/1996 | Baker | |
| 6,030,553 A * | 2/2000 | Huang et al. | 252/520.3 |
| 6,326,215 B1 | 12/2001 | Keen | |
| 6,506,296 B2 | 1/2003 | Babes-Dornea | |
| 6,655,010 B1 | 12/2003 | Hatfield | |
| 6,699,667 B2 | 3/2004 | Keen | |
| 6,737,286 B2 | 5/2004 | Tao | |

(Continued)

FOREIGN PATENT DOCUMENTS

| | | |
|---|---|---|
| EP | 08756225.2 | 3/2010 |
| WO | WO 2008/088780 | 7/2008 |
| WO | WO 2008/148025 | 12/2008 |

OTHER PUBLICATIONS

PCT authorized officer Lee W. Young, PCT/US/08/64744 International Search Report mailed Aug. 11, 2008, 11 pages.

(Continued)

*Primary Examiner* — Alex Noguerola
(74) *Attorney, Agent, or Firm* — George A. Leone; Citadel Patent Law

(57) ABSTRACT

An integrated sensing device is capable of detecting analytes using electrochemical (EC) and electrical (E) signals. The device introduces synergetic new capabilities and enhances the sensitivity and selectivity for real-time detection of an analyte in complex matrices, including the presence of high concentration of interferences in liquids and in gas phases.

18 Claims, 4 Drawing Sheets

U.S. PATENT DOCUMENTS

| | | |
|---|---|---|
| 6,773,926 B1 | 8/2004 | Freund |
| 7,030,452 B2 | 4/2006 | Tao |
| 7,357,851 B2 * | 4/2008 | Reid et al. ............... 204/403.04 |
| 7,655,128 B2 * | 2/2010 | Hsu et al. ..................... 205/775 |
| 7,955,492 B2 * | 6/2011 | Fujiwara et al. ........... 205/777.5 |
| 2002/0015963 A1 | 2/2002 | Keen |
| 2002/0090632 A1 | 7/2002 | Buck |
| 2003/0079999 A1 | 5/2003 | Penner |
| 2004/0023253 A1 | 2/2004 | Kunwar |
| 2004/0067646 A1 | 4/2004 | Tao |
| 2004/0104129 A1 | 6/2004 | Gu |
| 2004/0169243 A1 | 9/2004 | Tao |
| 2007/0054317 A1 | 3/2007 | Diebold |
| 2010/0056892 A1 * | 3/2010 | Ben-Barak et al. ........... 600/354 |

OTHER PUBLICATIONS

Bogozi, A., et al., "Molecular Adsorption onto Metallic Quantum Wires," J. Am. Soc. 2001, 123, pp. 4585-4590, American Chemical Society. USA.

Boussaad, S. et al., "Atom-size gaps and contacts between electrodes fabricated with a self-terminated electrochemical method," Applied Physics Letters, pp. 2398-2400, vol. 80, No. 13, Apr. 1, 2002, American Institute of Physics. USA.

Favier, F., et al., "Hydrogen Sensors and Switches from Electrodeposited Palladium Mesowire Arrays," Science, vol. 293, pp. 2227-2231, Sep. 21, 2001. USA.

Garcia, N. et al., "Magnetoresistance in excess of 200% in Ballistic Ni Nanocontacts at Room Temperature and 100 Oe," Physical Review Letters, vol. 82, No. 14, pp. 2923-2926, Apr. 5, 1999, American Physical Society. USA.

Handley, J. "Stretching the Wire Frontier," Apr. 1, 2002, pp. 196A-199A, vol. 74, Issue 7. USA.

Kim, S. et al., "Development of 3-D focus-ion-beam (FIB) etching method for nano and micro technology application", Microprocesses and Nanotechnology Conference 2001 International, pp. 34-35. USA.

Klep, I. et al., "Technology of silicon nano- and microelectrode array for pollution control", Semiconductor Conference 2001, CAS 2001 Proceedings International, vol., pp. 39-42. USA.

Li, C. et al., "Fabrication of stable metallic nanowires with quantized conductance," Nanotechnology 10, 1999, pp. 221-223, IOP Publishing, Ltd. UK.

Li, C., et al., "Molecular detection based on conductance quantization of nanowires," Applied Physics Letters, pp. 1333-1335, vol. 76, No. 10, Mar. 6, 2000, American Institute of Physics. USA.

Li, C., et al., "Quantum transport in metallic nanowires fabricated by electrochemical deposition/dissolution," Applied Physics Letters, pp. 894-896, vol. 72, No. 8, Feb. 23, 1998, American Institute of Physics. USA.

Morpurgo, A., et al., "Controlled fabrication of metallic electrodes with atomic separation," Applied Physics Letters, pp. 2084-2086, vol. 74, No. 14, Apr. 5, 1999, American Institute of Physics. USA.

Toriyama, S. et al., "Characteristics of silicon nano wire as piezoresistor for nano electro mechanical systems", Micro Electro Mechanical System 2001 MEMS 2001, 14.sup.th IEEE International Conference, pp. 305-308. USA.

* cited by examiner

SYSTEMS AND METHODS FOR INTEGRATED ELECTROCHEMICAL AND ELECTRICAL DETECTION

CROSS-REFERENCE TO RELATED APPLICATIONS

This application is a national phase application under 35 U.S.C. §371 of International Application No. PCT/US2008/064744 filed 23 May 2008, which claims priority to U.S. Provisional Patent Application Ser. No. 60/939,738 entitled, "Systems and Methods for Integrated Electrochemical and Electrical Detection" which was filed on May 23, 2007. The entire text of each of the above-referenced disclosures is specifically incorporated herein by reference without disclaimer.

BACKGROUND OF THE INVENTION

1. Field of the Invention

The present invention relates generally to sensors and, more particularly, to systems and methods for integrated electrochemical and electrical detection.

2. Description of Related Art

Electrochemical sensors have been used in various chemical and medical applications to detect concentrations of biological analyte. However, the inventors hereof have recognized that electrochemical detection is not without problems. For example, when an insufficient concentration of analyte is provided, the current flowing between working and counter electrodes of the sensor is undetectable. Because the amount of analyte detected is directly proportional to the current flowing through the sensor, small analyte concentration can result immeasurable.

Electrical sensors have also been used to determine analyte concentrations by detecting molecular binding-induced conductance or impedance changes in electrical materials (e.g., silicon, conducting polymers, and carbon nanotubes). Unfortunately, the inventors hereof have also identified many drawbacks of this technique. For instance, in addition to their large dimensions and high manufacturing costs, electrical sensors are generally highly dependent on the environment (e.g. ionic strength), less specific and less accurate.

The referenced shortcomings are not intended to be exhaustive, but rather are among many that tend to impair the effectiveness of previously known techniques as recognized by the present inventors. These problems are sufficient to demonstrate that the methodologies appearing in the art have not been satisfactory, and that a significant need exists for the techniques described and claimed in this disclosure.

SUMMARY OF THE INVENTION

An integrated sensing device is capable of detecting analytes using electrochemical (EC) and electrical (E) signals. The device introduces synergetic new capabilities and enhances the sensitivity and selectivity for real-time detection of an analyte in complex matrices, including the presence of high concentration of interferences in liquids and in gas phases.

In some embodiments, the invention relates to electrochemical-electrical (EC-E) sensors comprising: a first electrode fabricated on a substrate; a second electrode fabricated on the substrate and spaced apart from the first electrode; a bridging material coupling the first electrode to the second electrode; an electrolyte; a counter electrode; and a reference electrode; wherein at least one of the electrodes is connected to an electronic circuit for electrochemical-electrical control and/or measurement during use.

In specific embodiments, the first electrode of the sensor is connected to an electronic circuit for applying a potential perturbation to the first electrode during use. In some embodiments the electronic circuit is a biopotentiostat.

In some embodiments, one or more of the counter electrode, reference electrode, and/or bridging material is comprised on the substrate. However, in other embodiments one or more of these components will be comprised off the substrate.

In some specific embodiments, the sensor comprise a third electrode placed apart from the first and second electrodes. In some applications, the third electrode is employed for electrochemical control and/or measurement during use. Further, in embodiments with the third electrode, the first and second electrodes may be employed for conductance measurement during use. In some cases, the electronic circuit is a tripotentiostat.

The sensors can have a surface area ratio between the second electrode and the first electrode allows an electrochemical process taking place on the second electrode and electrical properties between the first and second electrodes to be controlled and/or measured simultaneously.

The bridging material may be any suitable material as understood by a person of ordinary skill in the art, whether now existing or yet to be discovered. For example, the bridging material may be, but it is not limited to, a polymer, Si, GaAs, a metal oxide, other organic and inorganic semiconductors, a molecularly imprinted material, and/or composites made of polymers and conducting or semiconducting materials. Further, the bridging material may be provided in the form or a nanotube, a nanowire, a nanoparticle, a nanorod, and/or a nanobelt.

In one particularly specific embodiment, an electrochemical-electrical (EC-E) sensor comprises a first electrode fabricated on a substrate and coupled to a biopotentiostat circuit for applying a potential perturbation to the first electrode, a second electrode fabricated on the substrate and spaced apart from the first electrode, a bridging material fabricated on the substrate and coupling the first electrode to the second electrode, a counter electrode fabricated on the substrate and operable to close an electric circuit, and a reference electrode fabricated on the substrate and operable to control a potential of at least one of the first and second electrodes. A surface area ratio between the second electrode and the first electrode allows an electrochemical process taking place on the second electrode and electrical properties between the first and second electrodes to be measured simultaneously.

Some aspects of the invention relate to methods comprising: providing an EC-E sensor as described above or in the claims; providing an analyte; detecting a byproduct; determining a conductance and/or electrical current of the conducting or semiconducting material; determining an electrochemical signal; and detecting the analyte employing the conductance and the electrochemical signal. In some embodiments, the conductance and/or electrical current can be measured using the first electrode. Further, in some embodiments, the electrochemical signal is measured using the second electrode. Such methods may further comprise adjusting the surface area ratio between the second electrode and the first electrode to optimize performance of the EC-E sensor. In some cases the may comprise a molecule in gas phase; in others, the analyte may comprises a molecule in liquid phase.

The term "coupled" is defined as connected, although not necessarily directly, and not necessarily mechanically.

The terms "a" and "an" are defined as one or more unless this disclosure explicitly requires otherwise.

The term "substantially," "about," and their variations are defined as being largely but not necessarily wholly what is specified as understood by one of ordinary skill in the art, and in one non-limiting embodiment, the substantially refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The invention and the various features and advantageous details are explained more fully with reference to the non-limiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only and not by way of limitation. Various substitutions, modifications, additions, and/or rearrangements within the spirit and/or scope of the underlying inventive concept will become apparent to those skilled in the art from this disclosure.

The present invention comprises systems and methods for integrated electrochemical and electrical detection. In one embodiment, the present invention integrates electrochemical and electrical (EC-E) sensing elements into a single device operable to simultaneously perform electrochemical and electrical detection, thus providing new capabilities compared to the single detection mode typically provided by existing sensors. The EC-E sensors disclosed herein provide unique selectivity features for real-time analyte detection in liquids, gases, cultures, tissues, and the like.

In one embodiment, an EC-E sensor may be able to detect an analyte either via electrochemical current changes ($\Delta I_{ec}$) of a conducting or semiconducting material, conductance changes of the conducting or semiconducting material ($\Delta G$), or a combination of both. The combination of both parameters ($\Delta I_{ec}$, $\Delta G$) is particularly advantageous because it enhances selectivity for detection of analytes in complex matrices, even in the presence of interferants with much higher concentrations than the concentration of the analyte. In some embodiments, a nanoscale version of the EC-E sensor may allow for the detection of very low concentrations of analytes.

Figure 1:
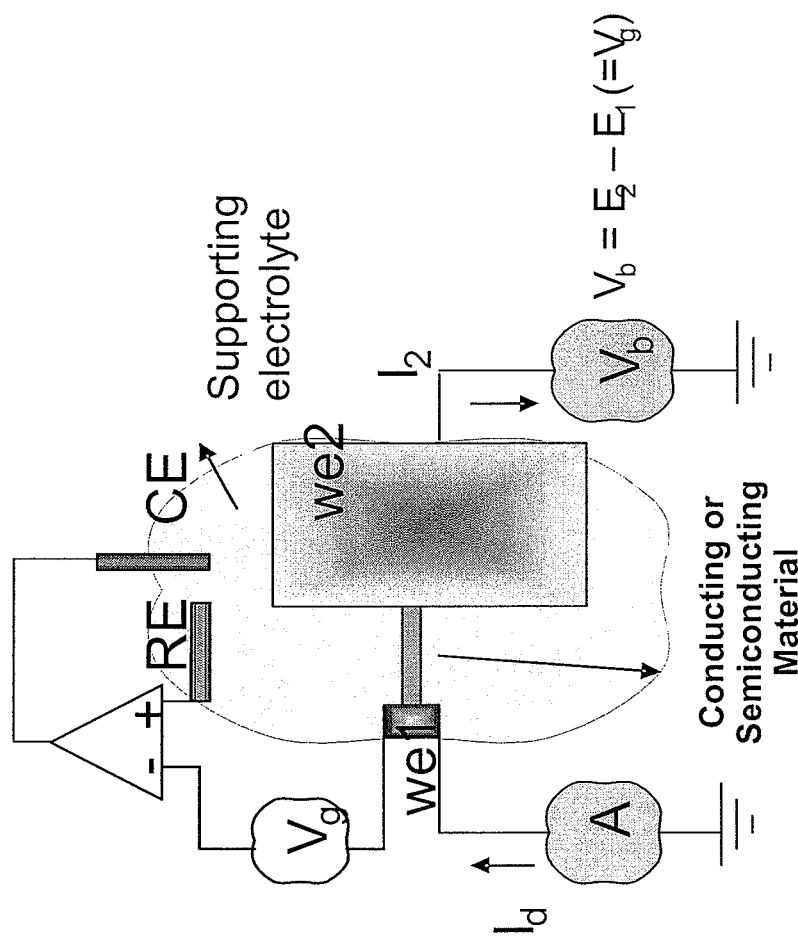
FIG. 1 shows a diagram of an EC-E sensor in accordance with embodiments of the present invention.

FIG. 1 shows a diagram of an EC-E sensor in accordance with embodiments of the present invention. The EC-E sensor may include a pair of asymmetric working electrodes WE1 and WE2 fabricated on a silicon chip or other suitable substrate. In one embodiment, electrodes WE1 and WE2 may have different surface areas, and may be separated by a gap varying from, for example, microns to nanometers. For example, WE2 may have a larger area compared to WE1. The surface area ratio (WE2/WE1) is advantageous when it becomes necessary to decrease a contribution of electrochemical and capacitive currents from WE1 ($I_{1,ec}$) on the drain current ($I_1$) taken from WE1, where $I_1$ may be approximately equal to $I_d$, which may be directly proportional to the conductance (G). Further, the surface area ratio (WE2/WE1) may increase an electrochemical product concentration produced on WE2, and thus it may improve the sensitivity to electrochemical current obtained from WE2 ($I_{2,ec}$). In operation, WE1 and WE2 may represent source and drain (working) electrodes. A bias potential ($V_b$) may be applied between WE2 and WE1.

The EC-E sensor may also include a counter electrode (CE) to close the electrical circuit responsible for the electrochemical currents. The amplifier (A) of FIG. 1 represents part of the bipotentiostat circuit used to apply potential perturbation on WE1, which is measured against a reference electrode (RE).

Referring again to FIG. 1, a conducting or semiconducting material may bridge the two electrodes. Examples of conducting material include conducting polymers, metal oxides, nanostructures (e.g., nanotubes, nanowires, nanoparticles, nanorods, nanobelts, nanoparticles, or molecularly imprinted materials). Alternatively or in addition to the above, conducting materials may include composites made of polymers and conducting or semiconducting materials. The conducting material may allow for the detection of electrical current through the material between the two electrodes WE1 and WE2 under a bias voltage ($V_b$).

The sensibility of conductance changes on the conducting or semiconducting material may be increased with a higher surface to volume ratio. This situation is reached when small but continuous and stable amounts of conducting material are immobilized or deposited into the gap. For example, use of few polymer strands, nanowires and nanotubes allows detection of conductance changes from concentrations of analytes as low a pM.

Conductivity measurements of the conducting or semiconducting material may also be performed through a drain current ($I_d$) from first electrode (WE1). An electrolyte may be provided to the device may give electrolytic conductance to the device. The supporting electrolyte may be liquid, polymer, semi-liquid or solid and may be composed of ionic liquids or solid or of gels or aqueous or organic ionic solutions. The supporting electrolyte may be held by a cell in intimate contact with the device surface. The second electrode (WE2) may be used to determine the electrochemical reduction/oxidation of analytes or analyte derivatives. An electrochemical potential ($E1=V_g$), may be applied between the drain electrode (WE1) and a reference electrode (RE) coupled to a supporting electrolyte. Moreover, $V_g$ may be gated through the supporting electrolyte from the reference electrode (RE) and electrochemical measurements may be monitored from a differential current between the electrodes determined by:

$$I_{2,ec}=I_2-I_d \qquad \text{Eq. 1}$$

where $I_2$ is this the current from WE2 as pictured in FIG. 1.

The sensitivity of the EC-E sensor may be adjusted and the selectivity may be further improved by optimizing, for example, the geometry and dimension of the electrodes, the length of the gap, amount and geometry of conducting material bridging the gap, chemical modification, as well as gate and bias potential control. For example, the geometry and dimension of the WE1 and WE2 electrodes, and in particular, the area ratio (WE2/WE1), may be altered and improved through an electrochemical selective deposition of metal on the second electrode (WE2). Several metals such as gold, platinum, palladium, mercury, nickel, silver, copper, cadmium, zinc, etc. may be suitable. By adjusting the geometry and dimension of WE1 and WE2, the electrodes' roughness and area may increase and allow for a reduction of the gap size from few micrometers to a few hundreds or a few nanometers.

Figure 2:
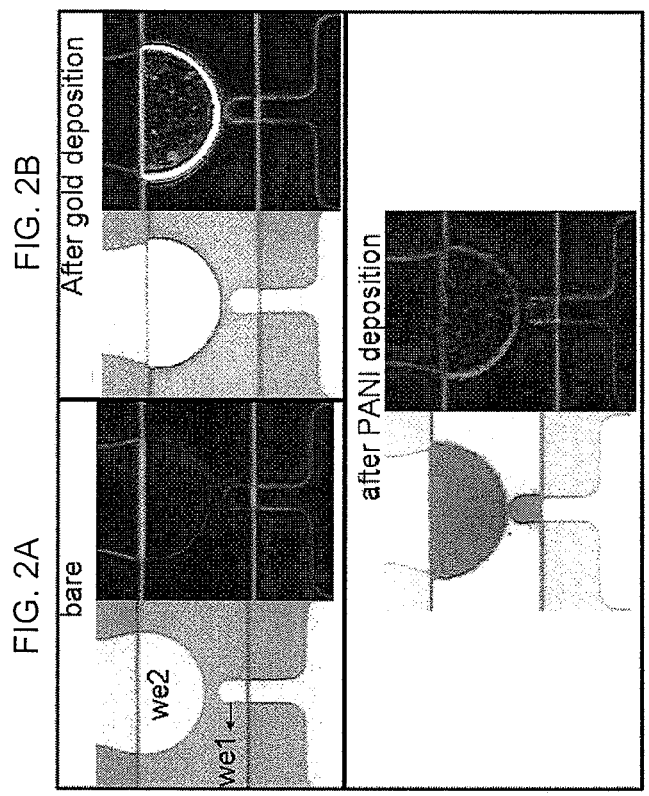
FIGS. 2A-2C show a bare sensor, a sensor after a metal deposition, and a sensor after a polymer deposition, in accordance with embodiments of the present invention.

FIGS. 2A and 2B show optical back and dark field images of a device before and after a metal electrodeposition of gold to enlarge the surface area of WE2, respectively. FIG. 2C shows the device of FIG. 2A after a polymer deposition. The higher brightness shown in FIG. 2B indicates increasing roughness of the WE2. It should be noted that the gap between WE1 and WE2 decreases in size as the surface area of WE2 increases. In some embodiments, smaller gaps between WE1 and WE2 may provide better sensitivity for electrical detection although the exact dimensions may depend upon the particular application.

The EC-E selectivity enhancement may vary based on the properties of the conducting material across the two electrodes WE1 and WE2. Alternatively, modification of the conducting material, electrode surface, chip surface, substrate surface, or the use of a supporting electrolyte with redox mediator molecules or other organic or biological recognizing elements, such as, but not limited to, cyclodextrins, crown ethers, peptides, proteins, enzymes, antibodies, aptamers, nucleic acids and peptide nucleic acids able to interact chemically or stereo-selectively with the analyte may be used to enhance the selectivity of the EC-E sensor. In one respect, the supporting electrolyte may be liquid or semi-solid or solid and chemically modified to avoid interferents.

In one embodiment, the present invention provides for the integration of many EC-E sensors on single chip or substrate. For a single analyte detection, even when materials and modification of the chip is uniform all over its multiple parallel devices, gated and biased potential control on different devices allows obtaining a combination of pair of conductance and electrochemical signals ($\Delta I_{ec}$, $\Delta G$) that ensures discrimination of analyte of interest in complex matrices.

FIGS. 3A-3G show diagrams of several reaction pathways that may be accounted and applied to EC-E detection in liquid or gas phases according to certain embodiments of the present invention. The following outlines the type of detection, the analyte, and the effect on the conducting or semiconducting material.

Case A: Independent Electrical-Electrochemical (E-EC) Detection

Figure 3:
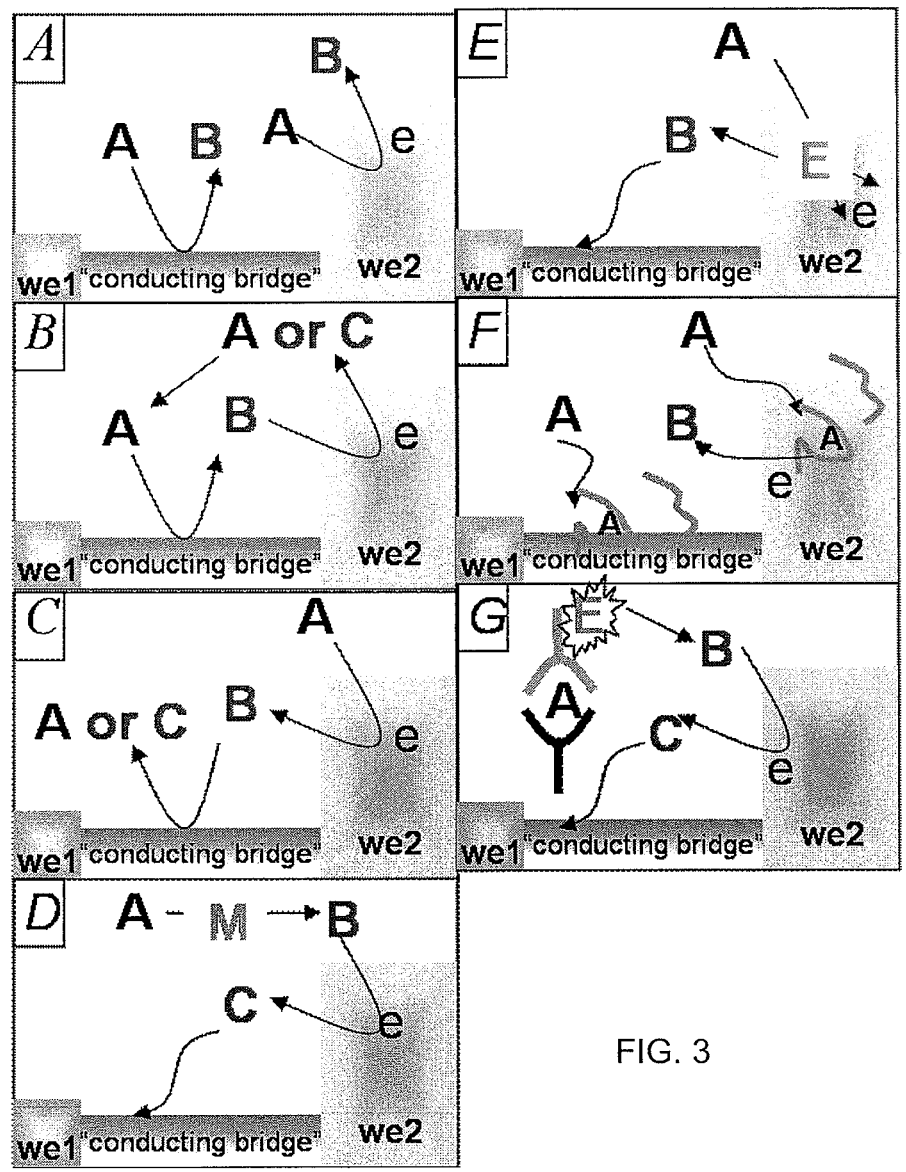
FIGS. 3A-3G show diagrams of EC-E sensors used in different applications, in accordance with embodiments of the present invention.

Referring to FIG. 3A, when analyte A is electrochemically active and irreversible arrives to the device surface, the analyte may modify the conductance of the conducting or semiconducting material ("conducting or semiconducting bridge") and may be electrochemically irreversible reduced or oxidized on WE2, providing independent drain current ($I_d$) and electrochemical current ($I_{2,ec}$) changes. One example is the detection of ascorbic acid.

Case B: Dependent Electrical-Electrochemical (E-EC) Detection

Referring to FIG. 3B, analyte A may be chemically converted to B in the conducting or semiconducting material and may electrochemically oxidize or reduce to another product C or revert back to B (if it is electrochemical reversible species). Chemical conversion of A to B may be induced by chemical modification of the conducting or semiconducting bridge or when conducting or semiconducting bridge native material is sensitive to redox changes from A.

Case C: Dependent Pure Electrical-Electrochemical (E-EC) Detection

Referring to FIG. 3C, analyte A may be oxidized or reduced electrochemically (EC detection) and the electrochemical product B may be detected on the conducting material (E detection). For example this reaction pathway may be used to detect nitro-explosives that produce intermediate reduction products that can oxidize or reduce the conducting or semiconducting material bridge. Additionally or alternatively, the detection of electroactive compounds of analyte A which may include reversible or quasi-reversible redox features in presence of interferences that are also electrochemically active (A') but irreversibly oxidized or reduced. Under this condition, only the electrochemical active product (B) coming from analyte of interest (A) may be electrically detected. For example, low dopamine concentrations (ranging from about a hundreds nM—to about a few micromolar range) can be detected in presence of high concentrations (mM range) of ascorbic acid, uric acid or other similar interferents. This detection scheme is referred to as an electrochemical-assisted electrical detection.

Case D: Chemical Mediated Electrochemical Electrical (EC-E) Detection

Referring to FIG. 3D, analyte A may be chemically transformed with assistance of mediator M, and then EC and E detected as described in FIGS. 3A-C described above. The chemical mediator may be dissolved in the supporting electrolyte (SE) or immobilized on the electrodes or chip surface. In one respect, analyte A may be acetone and may be detected using hydroxylamine as a mediator to produce an electrochemically active oxime derivative.

Case E: Redox Catalyst Mediated Electrochemical Electrical (EC-E) Detection

Referring to FIG. 3E, analyte A may be a catalyst target. An inorganic or biological catalyst may be chemically wired to the larger electrode (e.g., WE2) which may pump electrons for the regeneration of the catalyst. The catalyst byproduct may be detected on the conducting or semiconducting material, where the sensitivity for detection may be increased due to the catalytic effect. It is noted that a combination of catalysts may widen this application. For example, detection of aldehydes and alcohols may be made using quino-dehydrogenases immobilized on WE2. These enzymes produce acid products that can increase the conductance of pH sensitive conducting material.

Case F: Recognizing Element Mediated Electrochemical Electrical (EC-E) Detection Referring to FIG. 3F, electrodes and conducting material may be modified with an organic molecule, biomimic, or biological recognizing element which may selectively trap an analyte that may be electrochemically active. The active recognizing layer on WE2 serves as a preconcentrator of the analyte, which may be electrochemically oxidized or reduced. The recognition of the analyte on the conducting or semiconducting material may induce conformational, charge, or pH changes that may be transduced as a change in conductance. This particular case can be applied to, for example, the detection of heavy metal ions using peptides as probes.

Case G: Label-Dependent Electrochemical Electrical (EC-E) Detection

Referring to FIG. 3G, commercially available enzyme-labeled for detection of many hormones and tumor markers used in immunological assays combined with the application of EC-E detection may improve detection performance and to simplify instrumentation. Probes labeled with commonly used enzymes such as peroxidase and alkaline phosphate may be used to detect enzymatic products from antibodies immobilized on the EC-E devices which may have include a incubation of the sample. After rinsing and addition of enzyme reactants, the presence of enzyme may be developed by electrochemical detection of enzymatic products and conductance change due to oxidation of the conducting or semiconducting material. In cases where an unlabeled probe is immobilized on the conducting material, and in particular in the area bridging WE1 and WE2, the conductance changes may be detected directly during sample incubation. Later EC-E detection may subsequently be performed.

In one embodiment, a number of EC-E sensors may be applied to a multiple analyte detection in liquid and gas phases. Because integration of many devices may be achieved in on single chip, simultaneous monitoring of multiple analytes may be achieved by adjusting the chemical modification as well as gated and biased potentials. Detection of analytes in liquid phase involved delivery of the sample through injections to bath cell or through a microfluidic system, while detection of chemical vapors comprise diffusion gases through a supporting electrolyte layer.

Example

The following example is included to demonstrate specific embodiments of this disclosure. It should be appreciated by those of skill in the art that the techniques disclosed in the example that follows represent techniques discovered by the inventors to function in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the scope of the invention.

Figure 4:
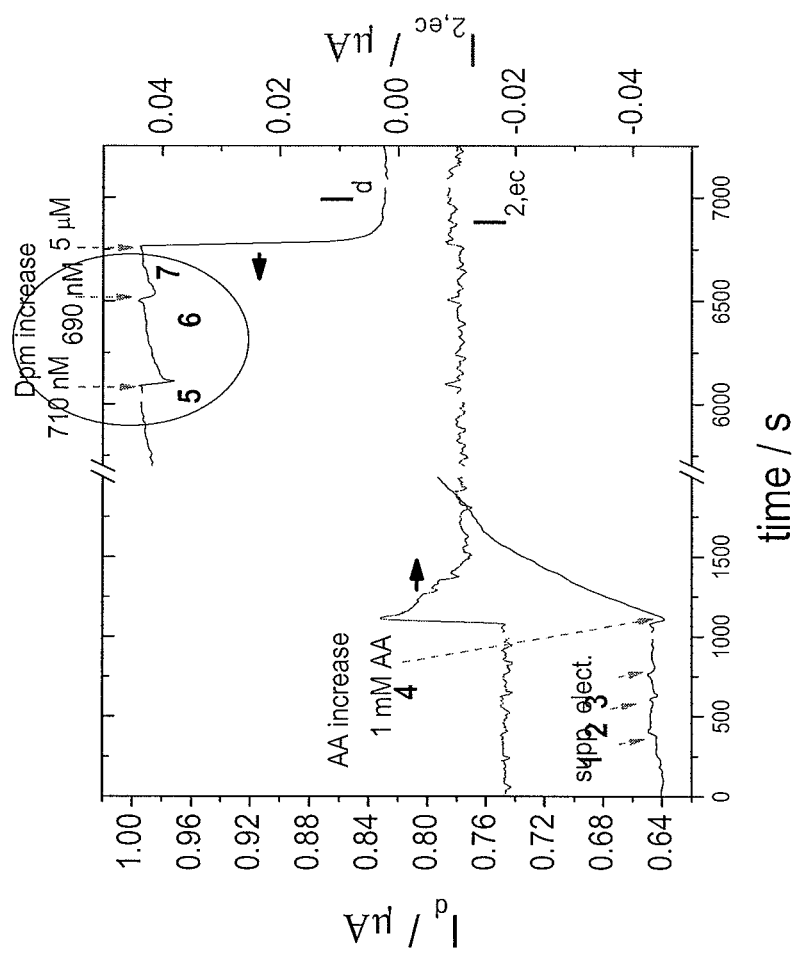
FIG. 4 shows a graph of an output of the EC-E sensor in accordance with embodiments of the present invention.

An illustrative, non-limiting experiment demonstrating the capability of EC-E nanosensor to detect the neurotransmitter dopamine (Dpm) in presence of its mayor physiological, ascorbic acid (AA), at a concentration level three orders of magnitude higher is shown. Referring to FIG. 4, the time course of EC-E sensor made of conducting bridge of polyaniline (e.g., as shown in FIG. 2C) is shown. Electrochemical current ($I_{2,ec}$) and drain ($I_d$) current are monitored simultaneously towards the injection of a supporting electrolyte (50 mM $H_2SO_4$), AA (1 mM), and Dpm (710 nM, 610 nM and 5 µM, respectively). It is noted that the voltages used in this examples are as follows: $V_g$=E1=200 mV vs Ag/AgCl and E2=450 mV vs Ag/AgCl.

Drain current ($I_d$) and electrochemical current from WE2 ($I_{ec,2}$) are simultaneously recorded during successive injections of the neurotransmitter "dopamine" (Dpm) (nanomolar (nM) or micromolar (uM) range) in the presence of three orders of magnitude higher concentration of ascorbic acid (AA). The experiments resembles physiological AA/Dpm concentration ratio. Initial injections of supporting electrolyte are performed to monitor stability of conducting bridge towards injections. No significant changes are observed due to injection and mechanical stirring itself. After that, AA concentration was injected to reach milimolar (mM) range. An increase of $I_d$ is observed in parallel with an increase of $I_{2,ec}$. The increase of $I_{2,ec}$ may be due to irreversible oxidation of AA to dehydroascorbic. The cause of $I_d$ changes may be due to the reduction of the polymer. Given the current experimental conditions, reduction of the conductor material is transduced into an increase of conductance (observed as important increase in $I_d$ over the time). This is an example of Case A previously described in the application cases.

Next, injections of Dpm performed after AA do not produce significant changes of electrochemical component current ($I_{2,ec}$) since electrochemical detection may not be sensitive to oxidation of hundred of nanomolar (nM) or micromolar (uM) range of Dpm. However, the electrochemical products of Dpm (dopaminoquinones, DQ) have an important effect on the conducting material, and thus $I_d$. DQ molecules are able to oxidized the conducting polymer material, and counteracts the reducing effect of AA, the mayor component in the media. Detection on a micromolar concentration change of Dpm are clearly observed by a sharp decrease of $I_d$, while detection of hundred of nanomolar concentration changes of Dpm may be less evident and may require better stabilization of baseline conditions to be addressed. This is an example of EC-assisted E detection described above.

Concentrations of a neurotransmitter three order of magnitude smaller than its mayor physiological interferent (AA) can be easily and continuously detected with the sensor of the present disclosure.

All of the methods disclosed and claimed herein can be executed without undue experimentation in light of the present disclosure. While the methods of this disclosure may have been described in terms of preferred embodiments, it will be apparent to those of ordinary skill in the art that variations may be applied to the methods and in the steps or in the sequence of steps of the method described herein without departing from the concept, spirit and scope of the disclosure. All such similar substitutes and modifications apparent to those skilled in the art are deemed to be within the spirit, scope, and concept of the disclosure as defined by the appended claims.

The invention claimed is:

1. An electrochemical-electrical (EC-E) sensor comprising:
   a first electrode fabricated on a substrate; a second electrode fabricated on the substrate and spaced apart from the first electrode;
   a bridging material coupling the first electrode to the second electrode; an electrolyte;

a counter electrode; and a reference electrode; and wherein at least one of the electrodes is connected to an electronic circuit for electrochemical-electrical control and/or measurement during use, and where a surface area ratio between the second electrode and the first electrode allows an electrochemical process taking place on the second electrode and electrical properties between the first and second electrodes to be controlled and/or measured simultaneously.

2. The sensor of claim 1, wherein the first electrode is connected to an electronic circuit for applying a potential perturbation to the first electrode during use.

3. The sensor of claim 2, wherein the electronic circuit is a biopotentiostat.

4. The sensor of claim 1, wherein the counter electrode is fabricated on the substrate.

5. The sensor of claim 1, wherein the reference electrode is fabricated on the substrate.

6. The sensor of claim 1, wherein the bridging material is fabricated on the substrate.

7. The sensor of claim 1, further comprising a third electrode placed apart from the first and second electrodes.

8. The sensor of claim 7, wherein the third electrode is employed for electrochemical control and/or measurement during use.

9. The sensor of claim 7, wherein the first and second electrodes are employed for conductance measurement during use.

10. The sensor of claim 7, wherein the electronic circuit is a tripotentiostat.

11. The sensor of claim 1, wherein the bridging material comprises a polymer, Si, GaAs, a metal oxide, and other organic and inorganic semiconductors, a nanostructure, a molecularly imprinted material, and composites made of polymers and conducting or semiconducting materials.

12. The sensor of claim 1, wherein the bridging material comprises at least one nanotube, nanowire, nanoparticle, nanorod, or nanobelt.

13. A method comprising:
providing an EC-E sensor of claim 1 including a conducting bridge made from a conducting or semiconducting material;
providing an analyte;
detecting a catalyst byproduct;
determining a conductance and/or electrical current of the conducting or semiconducting material;
determining an electrochemical signal; and
detecting the analyte employing the conductance and the electrochemical signal.

14. The method of claim 13, wherein the conductance and/or electrical current is measured using the first electrode.

15. The method of claim 13, wherein the electrochemical signal is measured using the second electrode.

16. The method of claim 13, wherein the step of providing the EC-E sensor further comprises adjusting a surface area ratio between the second electrode and the first electrode to optimize performance of the EC-E sensor.

17. The method of claim 13, wherein the analyte comprises a molecule in gas phase.

18. The method of claim 13, wherein the analyte comprises a molecule in liquid phase.

* * * * *